(12) United States Patent
Takahashi (10) Patent No.: US 8,623,299 B2
(45) Date of Patent: Jan. 7, 2014

(54) TISSUE TREATING APPARATUS

(75) Inventor: Kenji Takahashi, Chikuma (JP)

(73) Assignees: Sakura Seiki Co., Ltd., Nagano (JP); Sakura Finetek Japan Co., Ltd., Tokyo (JP)

( * ) Notice: Subject to any disclaimer, the term of this patent is extended or adjusted under 35 U.S.C. 154(b) by 65 days.

(21) Appl. No.: 13/119,949

(22) PCT Filed: Sep. 17, 2009

(86) PCT No.: PCT/JP2009/066251
§ 371 (c)(1),
(2), (4) Date: Mar. 18, 2011

(87) PCT Pub. No.: WO2010/035685
PCT Pub. Date: Apr. 1, 2010

(65) Prior Publication Data
US 2011/0171088 A1    Jul. 14, 2011

(30) Foreign Application Priority Data

Sep. 26, 2008 (JP) ................................ 2008-247422

(51) Int. Cl.
*A61B 10/00* (2006.01)

(52) U.S. Cl.
USPC ................. 422/536; 422/63; 422/64; 422/65; 422/66; 422/67; 436/180

(58) Field of Classification Search
USPC ......... 422/50, 501–503, 536, 63–67; 436/180
See application file for complete search history.

(56) References Cited

U.S. PATENT DOCUMENTS 3,892,197 A * 7/1975 Kinney et al. ................. 118/667

FOREIGN PATENT DOCUMENTS

| JP | 5849245 | 4/1983 |
|---|---|---|
| JP | 05149846 | 6/1993 |
| JP | 11271194 | 10/1999 |
| JP | 2001124679 | 5/2001 |

OTHER PUBLICATIONS

Sakura Seiki Co., Ltd., et al., International Search Report mailed Dec. 15, 2009 for PCT/JP2009/066251.

* cited by examiner

*Primary Examiner* — Jyoti Nagpaul
(74) *Attorney, Agent, or Firm* — Blakely Sokoloff Taylor & Zafman LLP (57) ABSTRACT

The present invention solves a problem of conventional tissue treating apparatuses: liquid chemicals which have been used given times and have become useless in a tissue specimen infiltration treatment and a cleaning liquid which has been used given times and has decreased in cleaning ability are required to be separately discarded/replaces. The tissue treating apparatus (10), which supplies given liquid chemicals to and discharges the same from a processing chamber (12) containing a tissue specimen so as to perform the tissue specimen infiltration treatment, comprises: liquid-chemical reservoirs (14, 16) for storing the liquid chemicals to be used in the infiltration treatment; cleaning-liquid reservoirs (19, 21) for storing the liquid chemicals which have become useless in the tissue specimen infiltration treatment and which are usable as cleaning liquids for removing a residual liquid chemical remaining in the processing chamber (12); and cleaning means for supplying the liquid chemicals in the cleaning-liquid reservoirs (19, 21) to and discharging the same from the processing chamber (12) so as to clean the inside of the processing chamber (12).

8 Claims, 8 Drawing Sheets

TISSUE TREATING APPARATUS

CROSS-REFERENCE TO RELATED APPLICATION

This is a non-provisional application claiming the benefit of International Patent Application No. PCT/JP2009/066251, filed Sep. 17, 2009.

FIELD OF TECHNOLOGY

The present invention relates to a tissue-treating apparatus, more precisely relates to a tissue-treating apparatus, in which a tissue specimen infiltration treatment is performed by supplying different kinds or different concentrations of liquid chemicals to and discharging the same from a processing chamber, in which a tissue specimen is contained, in a predetermined order.

BACKGROUND OF TECHNOLOGY

In hospitals and laboratories, tissue treating apparatuses, in each of which tissue specimens are automatically fixed, dehydrated, degreased, replaced and embedded in paraffin, are used for producing microscopic specimens of tissue specimens taken from living bodies.

Figure 9:
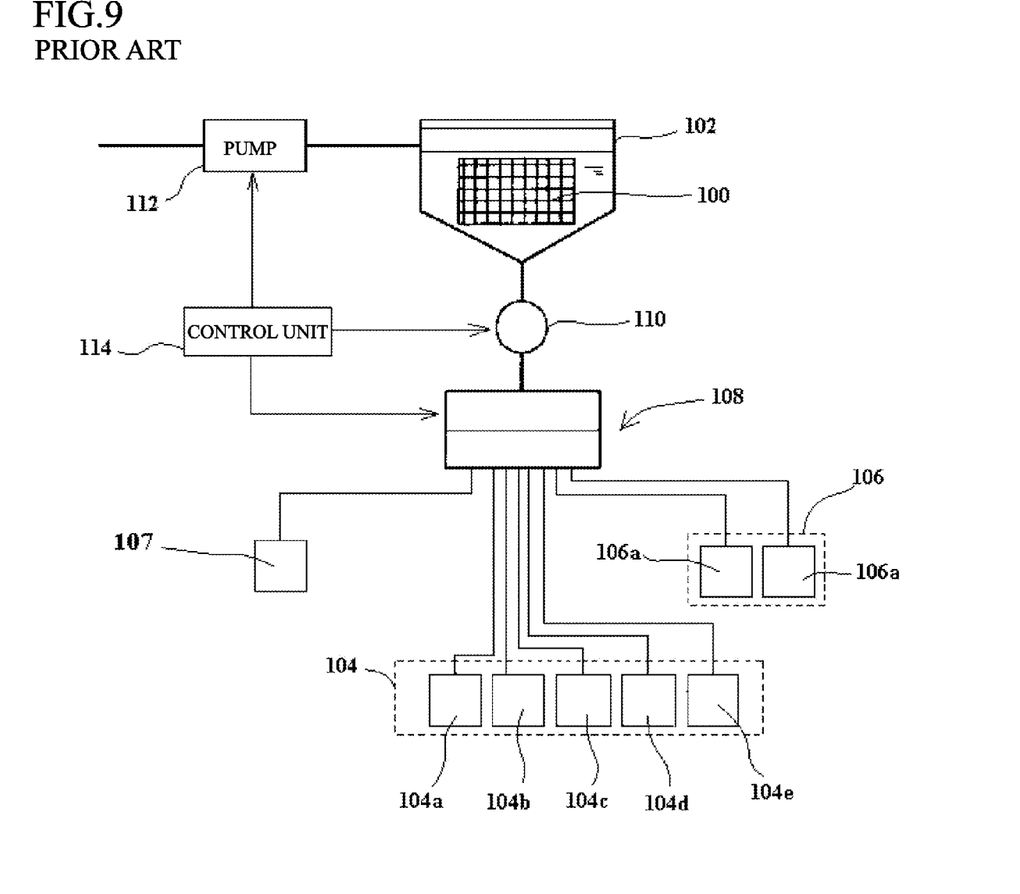
FIG. 9 is a schematic view of the conventional tissue treating apparatus.

For example, a conventional tissue treating apparatus is shown in FIG. 9. In the tissue treating apparatus shown in FIG. 9, a main body of the apparatus includes: a processing chamber 102 accommodating baskets 100, in which tissue specimens are contained; a plurality of liquid-chemical reservoirs 104a-104e being mounted on a rack 104 and storing liquid chemicals, with sequentially different concentrations, for performing an infiltration treatment of the tissue specimens in the baskets 100; and paraffin reservoirs 106a and 106b accommodated in a heat-retaining chamber 106. As to the liquid-chemical reservoirs 104a-104b, concentrations of the liquid chemicals in the liquid-chemical reservoirs 104a-104e are 104a<104b<104c<104d<104e (numbers of times of using the liquid chemicals are 104a>104b>104c>104d>104e).

Each of the liquid-chemical reservoirs 104a-104e and the paraffin reservoirs 106a and 106b is connected to a rotary valve 108 provided to the main body as a selection valve, and the rotary valve 108 is connected to the processing chamber 102 via an open/close valve 110.

With this structure, each of the liquid-chemical reservoirs 104a-104e and the paraffin reservoirs 106a and 106b is selectively connected to the processing chamber 102 by the rotary valve 108.

Further, inner pressure of the processing chamber 102 is increased and reduced by a pump 112, and the liquid chemical or paraffin can be supplied to the processing chamber 102 from one of the liquid-chemical reservoirs 104a-104e and the paraffin reservoirs 106a and 106b, which is selected by the rotary valve 108, in a state where the inner pressure of the processing chamber 12 is reduced.

The liquid chemical or paraffin, which has been supplied to the processing chamber 102 and brought into contact with the tissue specimens in the basket 100, is returned to the original reservoir by increasing the inner pressure of the processing chamber 102 by the pump 112.

Since the rotary valve 108, the open/close valve 110 and the pump 112 are controlled by a control unit 114, the tissue specimens are infiltrated in the given liquid chemicals and the paraffin according to a predetermined treatment sequence, which has been previously set in the control unit 114, and then the tissue specimens are infiltrated in the paraffin.

In the tissue treating apparatus shown in FIG. 9, the residual paraffin, which remains in the processing chamber 102 after completing the tissue specimen infiltration treatment, is cleaned by using a cleaning liquid stored in a cleaning-liquid reservoir 107 as described in Patent Document 1. Each of the liquid chemicals used for the infiltration treatment may be used as the cleaning liquid.

Patent Document 1: Japanese Laid-open Patent Publication No. 5-149846

SUMMARY OF THE INVENTION

In the tissue treating apparatus shown in FIG. 9, the residual paraffin, which remains in the processing chamber 102 after completing the tissue specimen infiltration treatment, can be cleaned and removed, and the tissue specimen infiltration treatment can be newly started in the processing chamber 102 in which no paraffin remains.

However, in the tissue treating apparatus shown in FIG. 9, the cleaning liquid is separately stored, from the liquid chemicals, in the dedicated cleaning-liquid reservoir 107.

If the liquid chemicals used in the tissue treating apparatus shown in FIG. 9 are used given times, the liquid chemicals will badly influence the completed tissue specimens. Thus, the liquid chemicals which have been used given times are discarded and replaced with new chemicals (new liquid chemicals) so as to secure qualities of the completed tissue specimens.

Cleaning ability of the cleaning liquid is drastically decreased after using the cleaning liquid given times, so the cleaning liquid too is discarded and replaced with a new cleaning liquid.

As described above, an operator must separately discard and replace the liquid chemicals for performing the tissue specimen infiltration treatment and the cleaning liquid for cleaning the processing chamber 102.

From the viewpoint of resource saving, it is wasteful to immediately discard the liquid chemicals which have been used given times and have become useless in the tissue specimen infiltration treatment.

An object of the present invention is to provide a tissue treating apparatus, which is capable of: solving the problem of the conventional apparatus, i.e., liquid chemicals, which have been used given times and have become useless in the tissue specimen infiltration treatment, and the cleaning liquid, which has been used given times and has decreased in cleaning ability, being required to be separately discarded/replaces; reusing the liquid chemicals, which have been used given times and have become useless in the tissue specimen infiltration treatment; and highly saving the trouble of discarding/replacing the liquid chemicals, which have become useless in the tissue specimen infiltration treatment, and the cleaning liquid, which has decreased in the cleaning ability.

The inventor of the present invention has studied to solve the above described problems, thus he performed the tissue specimen infiltration treatment, in the processing chamber 102 of the tissue treating apparatus shown in FIG. 9, in ethanol, xylene and paraffin in that order, and then the processing chamber 102 was cleaned by using the xylene to be discarded, which had been used given times, so that he found that the processing chamber 102 could be fully cleaned and he reached the present invention.

Namely, the tissue treating apparatus of the present invention, which supplies different kinds or different concentrations of liquid chemicals to and discharges the same, in a predetermined order, from a processing chamber containing a tissue specimen so as to perform a tissue specimen infiltration treatment, comprises: liquid-chemical reservoirs for storing the liquid chemicals to be used in the tissue specimen infiltration treatment; and a cleaning-liquid reservoir for storing liquid chemical which has become useless in the tissue specimen infiltration treatment and which is usable as a cleaning liquid for removing a residual liquid chemical remaining in the processing chamber, and cleaning means supplies the liquid chemical in the cleaning-liquid reservoir to and discharges the same from the processing chamber so as to clean the inside of the processing chamber.

The tissue treating apparatus may further comprise means for transferring the liquid chemical which has been used given times and have become useless in the tissue specimen infiltration treatment from the liquid-chemical reservoir to the cleaning-liquid reservoir. With this structure, the liquid chemical which has become useless in the tissue specimen infiltration treatment can be easily transferred to the cleaning-liquid reservoir.

The tissue treating apparatus may further comprise means for supplying the liquid chemical of an amount corresponding to an insufficiency of an amount of the cleaning liquid supplied from the liquid-chemical reservoir, in which the liquid chemical for the tissue specimen infiltration treatment is stored, when the amount of the cleaning liquid supplied from the cleaning-liquid reservoir to the processing chamber is insufficient. With this structure, the processing chamber can be continuously cleaned without discontinuation.

The tissue treating apparatus may further comprise means for discarding the liquid chemical from the cleaning-liquid reservoir to an external drain reservoir. With this structure, the cleaning liquid can be easily discarded from the cleaning-liquid reservoir to the external drain reservoir.

The tissue treating apparatus may further comprise: means for reducing inner pressure of the processing chamber; and means for heating the processing chamber. With this structure, the residual liquid chemical remaining in the processing chamber can be effective cleaned, and cleaning ability of the cleaning liquid can be improved by evaporating and removing low-boiling components.

The tissue treating apparatus may further comprise means for warming the liquid chemicals stored in the cleaning-liquid reservoirs. With this structure, the cleaning liquid supplied to the processing chamber can be warmed until reaching a predetermined temperature, so that an amount of time for cleaning the processing chamber can be shortened.

Further, in the tissue treating apparatus, ethanol, xylene and paraffin may be used as the liquid chemicals for the tissue specimen infiltration treatment performed in the processing chamber, and the liquid chemicals may be stored in the liquid-chemical reservoirs respectively; an ethanol cleaning liquid, which is the ethanol useless in the tissue specimen infiltration treatment, may be stored in a first cleaning-liquid reservoir, and a xylene cleaning liquid, which is the xylene useless in the tissue specimen infiltration treatment, may be stored in a second cleaning-liquid reservoir; and the cleaning means may firstly clean the inside of the processing chamber with the xylene cleaning liquid stored in the second cleaning-liquid reservoir, and then the cleaning means may clean the inside of the processing chamber with the ethanol cleaning liquid stored in the first cleaning-liquid reservoir. With this structure, the tissue specimen can be infiltration-treated, with ethanol, in the processing chamber from which paraffin and xylene have been sufficiently removed.

EFFECTS OF THE INVENTION

In the tissue treating apparatus of the present invention, the liquid chemical, which has become useless in the tissue specimen infiltration treatment but is capable of removing the residual chemical remaining in the processing chamber, can be stored in the cleaning-liquid reservoir as the cleaning liquid. The cleaning liquid in the cleaning-liquid reservoir can be used to remove the residual liquid chemical.

In the present invention, the liquid chemicals which have become useless in the tissue specimen infiltration treatment can be used to clean the processing chamber, so that effective use of the liquid chemicals can be realized.

The tissue treating apparatus of the present invention has the liquid-chemical reservoirs, which store the liquid chemicals being useless in the tissue specimen infiltration treatment, and the cleaning-liquid reservoir, which stores the used liquid chemical as the cleaning liquid. Therefore, the liquid chemical, which has become useless in the tissue specimen infiltration treatment, can be transferred to the empty cleaning-liquid reservoir, from which the cleaning liquid has been discarded, so that discarding/replacing the cleaning liquid can be performed.

Therefore, in comparison with the conventional tissue treating apparatus in which the liquid chemicals being useless in the tissue specimen infiltration treatment and the cleaning liquid having a poor cleaning ability are separately discarded/replaced, the liquid chemicals and cleaning liquid can be easily discarded/replaced in the tissue treating apparatus of the present invention.

EMBODIMENTS OF THE INVENTION

Figure 1A:
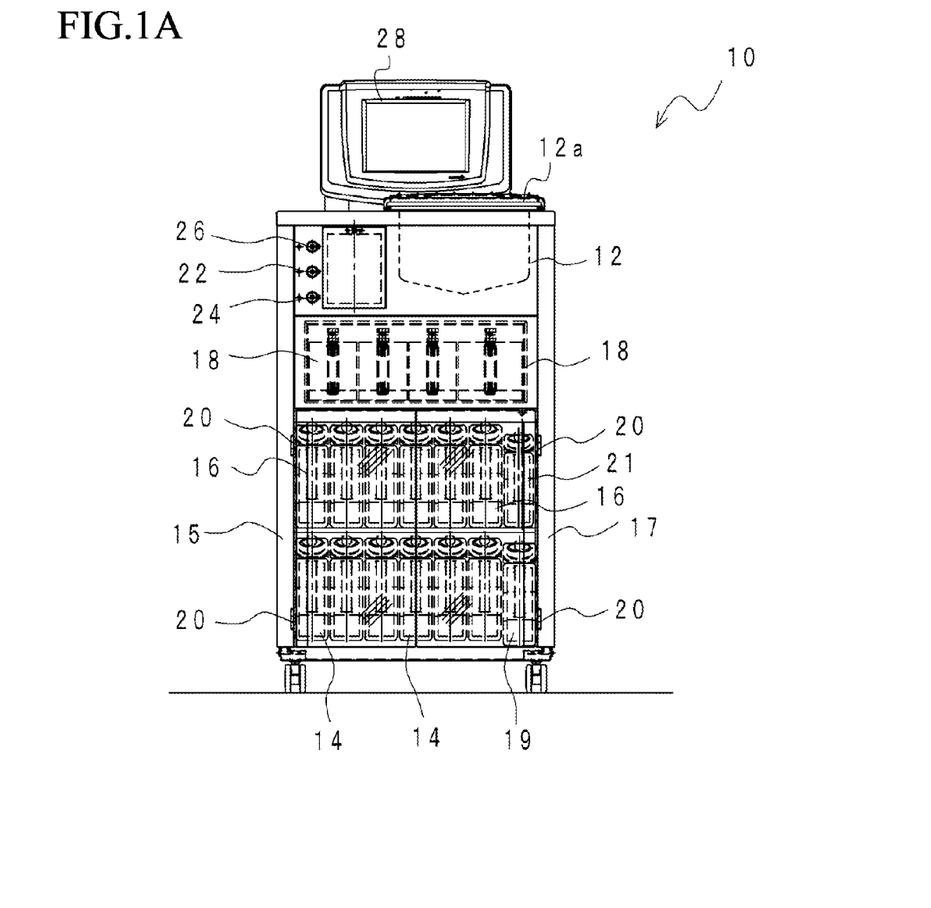
FIG. 1 includes a front view and a plan view of an embodiment of the tissue treating apparatus relating to the present invention.
Figure 1B:
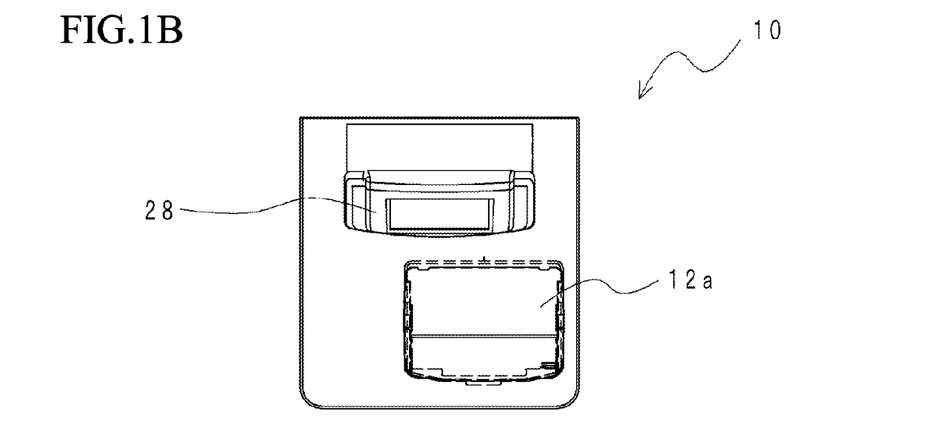
Figure 2:
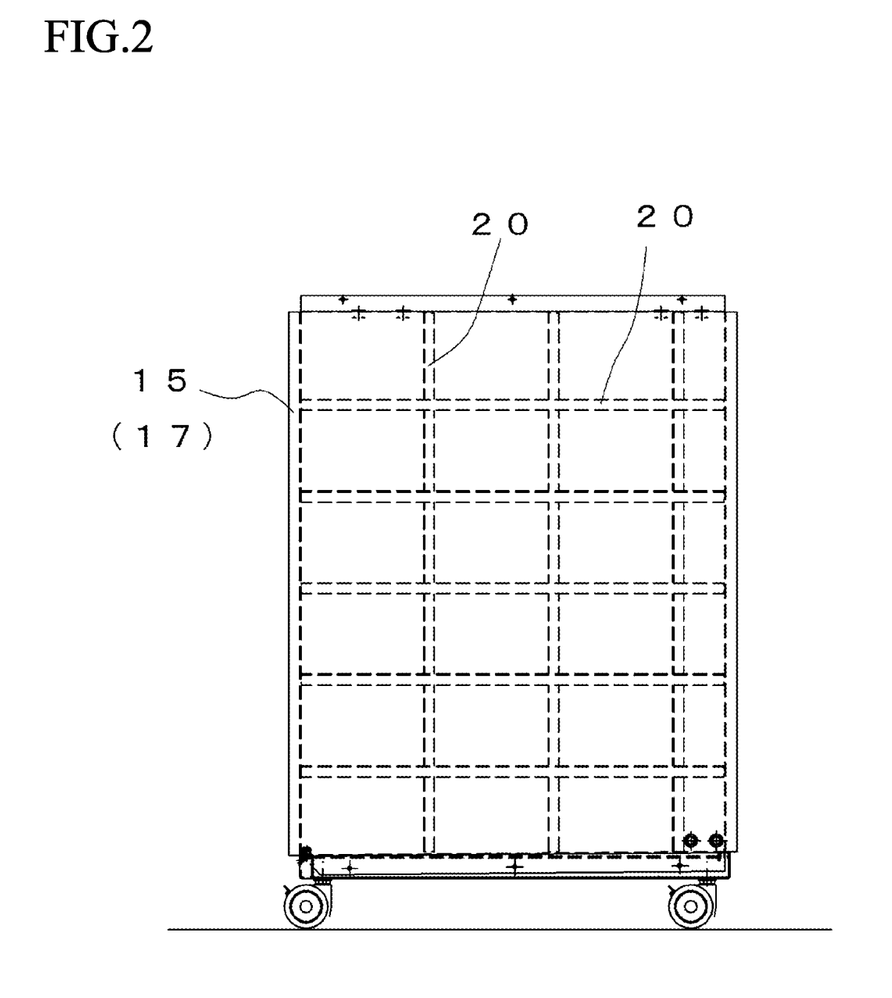
FIG. 2 is an explanation view explaining reinforcement of new liquid reservoirs of the tissue treating apparatus shown in FIG. 1.

An embodiment of the tissue treating apparatus relating to the present invention is shown in FIGS. 1 and 2. FIG. 1A is a front view of the tissue treating apparatus, and FIG. 1B is a plan view of the tissue treating apparatus.

In the tissue treating apparatus shown in FIG. 1, a processing chamber 12, in which baskets storing tissue specimens are accommodated, is opened and closed by a lid 12a. In the processing chamber 12, moisture in the tissue specimens is replaced by ethanol, and then xylene is supplied to replace ethanol in the tissue specimens by xylene, further molten paraffin is supplied to replace xylene in the tissue specimens by paraffin.

Thus, a plurality of liquid-chemical reservoirs 14, 14 . . . , in which ethanol to be supplied to the processing chamber 12, with different concentrations, are stored, are arranged in a lowermost part of a main body of the apparatus including the processing chamber 12. The ethanol having different concentrations are respectively stored in the liquid-chemical reservoirs 14, 14 . . . . And, a plurality of liquid-chemical reservoirs 16, 16 . . . , in which xylene to be supplied to the processing chamber 12, with different concentrations, are stored, are arranged in a second part above the lowermost part, in which the liquid-chemical reservoirs 14, 14 . . . are arranged. The xylene having different concentrations are respectively stored in the liquid-chemical reservoirs 16, 16 . . . .

Further, a plurality of liquid-chemical reservoirs 18, 18 . . . , in which molten paraffin to be supplied to the processing chamber 12 are stored respectively, are arranged in a third part above the second part, in which the liquid-chemical reservoirs 16, 16 . . . are arranged. The part accommodating the liquid-chemical reservoirs 18, 18 . . . is a heat-retaining chamber capable of maintaining a molten state of paraffin. Capacity of the rightmost liquid-chemical reservoir 18 of the liquid-chemical reservoirs 18, 18 . . . is larger than that of other liquid-chemical reservoirs 18, 18 . . . , and molten paraffin is stored therein.

An ethanol cleaning liquid, which is ethanol being useless in a tissue specimen infiltration treatment, is stored in a first cleaning-liquid reservoir 19 and a xylene cleaning liquid, which is xylene being useless in the tissue specimen infiltration treatment, is stored in a second cleaning-liquid reservoir 21 as cleaning liquids for cleaning the inside of the processing chamber 12.

A new chemical reservoir 15, whose capacity is larger than that of the liquid-chemical reservoirs 14, 14 . . . (e.g., twice or three times as large as the capacity of the liquid-chemical reservoirs 14, 14 . . . ) and in which unused new ethanol (new liquid chemical) is stored, is integrally attached to one of sidewall faces of the main body; a new chemical reservoir 17, whose capacity is larger than that of the liquid-chemical reservoirs 16, 16 . . . (e.g., twice or three times as large as the capacity of the liquid-chemical reservoirs 16, 16 . . . ) and in which unused new xylene (new chemical) is stored, is integrally attached to the other sidewall face of the main body. By integrally attaching the new chemical reservoirs 15 and 17 to the both sidewall faces, structural strength of the apparatus can be improved.

The new chemical reservoirs 15 and 17 have capacities larger than those of the liquid-chemical reservoirs 14, 14 . . . and 16, 16 . . . , and they are slimmer than the liquid-chemical reservoirs. As shown in FIG. 2, an inner wall face of each of the new chemical reservoirs 15 and 17 is reinforced by reinforcing members 20, 20 . . . , which are bonded crosswise. By reinforcing the inner wall face with the reinforcing members 20, 20 . . . , even if inner pressure of the new chemical reservoirs 15 and 17 are reduced when the new liquid chemicals are supplied to the new chemical reservoirs or the inner pressure (hydraulic head pressure) of the new chemical reservoirs are increased when prescribed amounts of ethanol and xylene are supplied to the new chemical reservoirs, deformation of the new chemical reservoirs 15 and 17 can be highly restrained.

Supply ports 22 and 24 for supplying the new liquid chemicals to the new chemical reservoirs 15 and 17 and a supply/discharge port 26 for supplying the liquid chemical to and discharging the same from the processing chamber 12 are provided in the front face of the main body of the tissue treating apparatus 10.

A display unit 28 is provided on the upper face of the main body of the apparatus 10 so as to show treating states of the tissue specimens in the processing chamber 12, etc.

Figure 3:
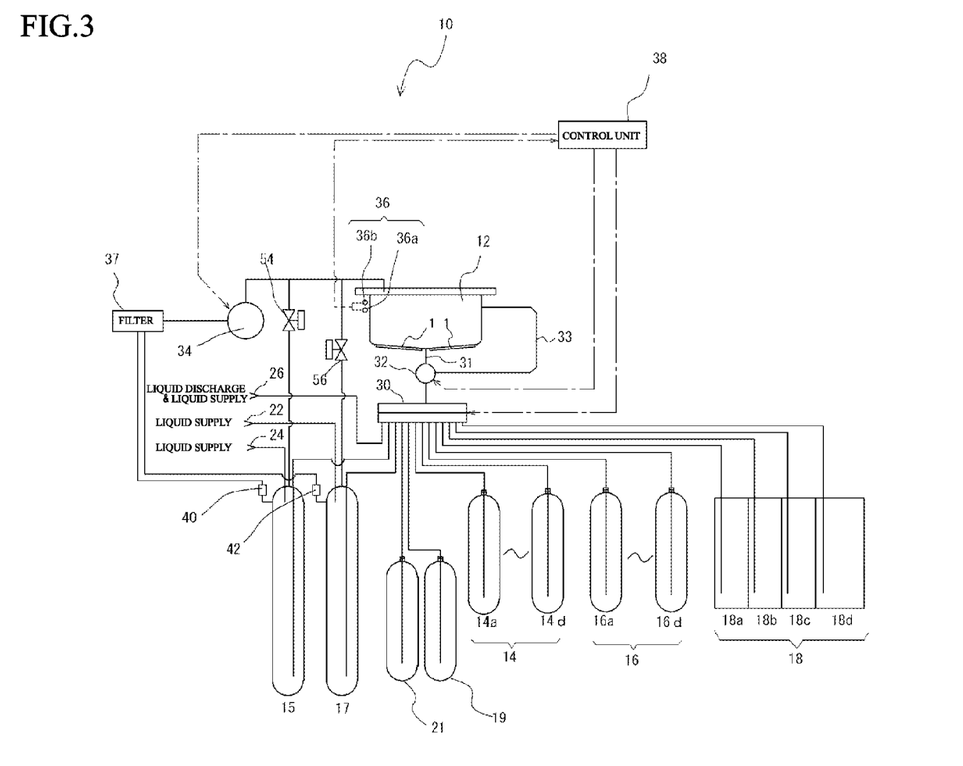
FIG. 3 is a systematic chart of the tissue treating apparatus shown in FIG. 1.

A schematic diagram of the tissue treating apparatus 10 shown in FIG. 1 is shown in FIG. 3. As shown in FIG. 3, the liquid-chemical reservoirs $14a$-$14d$ for storing ethanol and the liquid-chemical reservoirs $16a$-$16d$ for storing xylene are accommodated in the main body of the apparatus 10. Further, the liquid-chemical reservoirs $18a$-$18d$ for storing molten paraffin are accommodated therein, the capacity of the liquid-chemical reservoir $18d$ is larger than those of the liquid-chemical reservoirs $18a$-$18c$ so as to refill the liquid-chemical reservoirs $18a$-$18c$, in which molten paraffin of insufficient amounts have been stored, with the molten paraffin of the amount corresponding to the insufficiencies. When paraffin is supplied to the tissue treating apparatus, new paraffin is supply to the chemical reservoir $18d$.

The xylene cleaning liquid, which is the xylene being useless in the tissue specimen infiltration treatment, is stored in the second cleaning-liquid reservoir 21, and the ethanol cleaning liquid, which is the ethanol being useless in the tissue specimen infiltration treatment, is stored in the first cleaning-liquid reservoir 19.

As shown in FIG. 3, a rotary valve 30, which acts as a selection valve, is provided to the main body of the apparatus 10 so as to selectively connect the liquid-chemical reservoir, which is one selected from the liquid-chemical reservoirs $14a$-$14d$, $16a$-$16d$ and $18a$-$18d$ and which stores the liquid-chemical with a prescribed concentration, to the processing chamber 12.

The rotary valve 30 connects the processing chamber 12 to the first cleaning-liquid reservoir 19 or the second cleaning-liquid reservoir 21.

Note that, the molten paraffin stored in the liquid-chemical reservoir $18a$-$18d$ is supplied to the processing chamber 12, so a heater 11 is provided to a bottom part of the processing chamber 12 in order to heat the processing chamber 12 and maintain the molten state of the paraffin.

In the tissue treating apparatus shown in FIG. 3, concentrations of ethanol stored in the liquid-chemical reservoirs $14a$-$14d$ are $14a<14b<14c<14d$. Numbers of times of infiltrating tissue specimens in the ethanol stored in the liquid-chemical reservoirs $14a$-$14d$ and amounts of impurities, e.g., water, fat, remaining therein are $14a>14b>14c>14d$.

Concentrations of xylene stored in the liquid-chemical reservoirs $16a$-$16d$ are $16a<16b<16c<16d$ due to interfusion of ethanol.

The liquid-chemical reservoirs $18a$-$18d$ are arranged in the heat-retaining chamber, and concentrations of molten paraffin stored therein are $18a<18b<18c<18d$. Numbers of times of infiltrating tissue specimens in the paraffin stored in the liquid-chemical reservoirs $18a$-$18d$ and amounts of xylene interfused therein are $18a>18b>18c>18d$.

An open/close valve 32 is provided midway between a pipe 31, which is connected to a bottom face of the processing chamber 12 and the rotary valve 30, and a pipe 33 is connected to the open/close valve 32 and the upper part of the processing chamber 12. The open/close valve 32 is a three-way valve capable of connecting the pipe 31 to the rotary valve 30 and connecting the pipe 33 to the rotary valve 30.

A pump 34 is capable of increasing and reducing inner pressure of the processing chamber 12, and the liquid chemical or the cleaning liquid can be supplied to the processing chamber 12 from the prescribed liquid-chemical reservoir or cleaning-liquid reservoir, which has been selected by the rotary valve 30, by reducing the inner pressure of the processing chamber 12 by the pump 34 and connecting the prescribed liquid-chemical reservoir or cleaning-liquid reservoir to the pipe 33 by the open/close valve 32.

On the other hand, the liquid chemical stored in the processing chamber 12 can be sent to the prescribed liquid-chemical reservoir, which has been selected by the rotary valve 30, by increasing the inner pressure of the processing chamber 12 by the pump 34 and connecting the prescribed liquid-chemical reservoir to the pipe 31 by the open/close valve 32.

Therefore, the processing chamber 12, the pump 34, the rotary valve 30 and the open/close valve 32 can be used as means for transferring the liquid chemicals between the liquid-chemical reservoirs or between the liquid-chemical reservoirs and the cleaning-liquid reservoirs. Namely, after the liquid chemical stored in one of the liquid-chemical reservoirs is completely supplied to the processing chamber 12 via the rotary valve 30, the liquid chemical stored in the processing chamber 12 can be transferred to another liquid-chemical reservoir or cleaning-liquid reservoir.

Note that, the pump 34 is capable of sucking air through a filter 37 and discharging a gas including liquid chemicals from the processing chamber 12.

The processing chamber 12 has a detection sensor 36 for detecting that a prescribed amount of liquid chemical is supplied thereto. The detection sensor 36 is constituted by a level-securing sensor 36a and an upper limit sensor 36b. The level-securing sensor 36a is used for securing the amount of the liquid chemical in the processing chamber 12 so as to fully infiltrate the tissue specimens in the liquid chemical; the upper limit sensor 36b is used for detecting upper limit of the amount of the liquid chemical stored in the processing chamber 12.

The new chemical reservoirs 15 and 17 are respectively integrally attached to the both sidewall faces of the main body including the liquid-chemical reservoirs, the cleaning-liquid reservoirs, the rotary valve 30, the open/close valve 32, etc. The capacity of the new chemical reservoir 15 is twice or three times as large as that of the liquid-chemical reservoirs 14a-14d, and unused new ethanol is stored therein. The unused new ethanol can be supplied to the new chemical reservoir 15 via the supply port 24.

The capacity of the new chemical reservoir 17 is twice or three times as large as that of the liquid-chemical reservoirs 16a-16d, and unused new xylene is stored therein. The unused new xylene can be supplied to the new chemical reservoir 17 via the supply port 22.

Pressure equalizing lines are provided between the processing chamber 12 and the new chemical reservoirs 15 and 17, and open/close valves 54 and 56 are respectively provided to the pressure equalizing lines.

The chemicals in the new chemical reservoirs 15 and 17 are evaporated by outside air temperature, so inner pressures of the new chemical reservoirs 15 and 17 are increased. To keep the inner pressures, which are increased by the evaporating gas, below a prescribed pressure, safety valves 40 and 42 are provided and the evaporating gas is discharged through the filter 37 to get rid of foul odor.

As shown in FIG. 3, the tissue treating apparatus 10 has a control unit 38 for controlling the rotary valve 30, the open/close valve 32 and the pump 34. The control unit 38 firstly infiltrates the tissue specimens, which have been contained in the processing chamber 12, in ethanol so as to replace moisture and fat in the tissue specimens by ethanol. The tissue specimens are infiltrated in ethanol by the steps of: firstly supplying ethanol from the liquid-chemical reservoir 14a to the processing chamber 12; and sequentially supplying ethanol from the liquid-chemical reservoirs 14b, 14c and 14d to perform the tissue specimen infiltration treatment therein.

Figure 4:
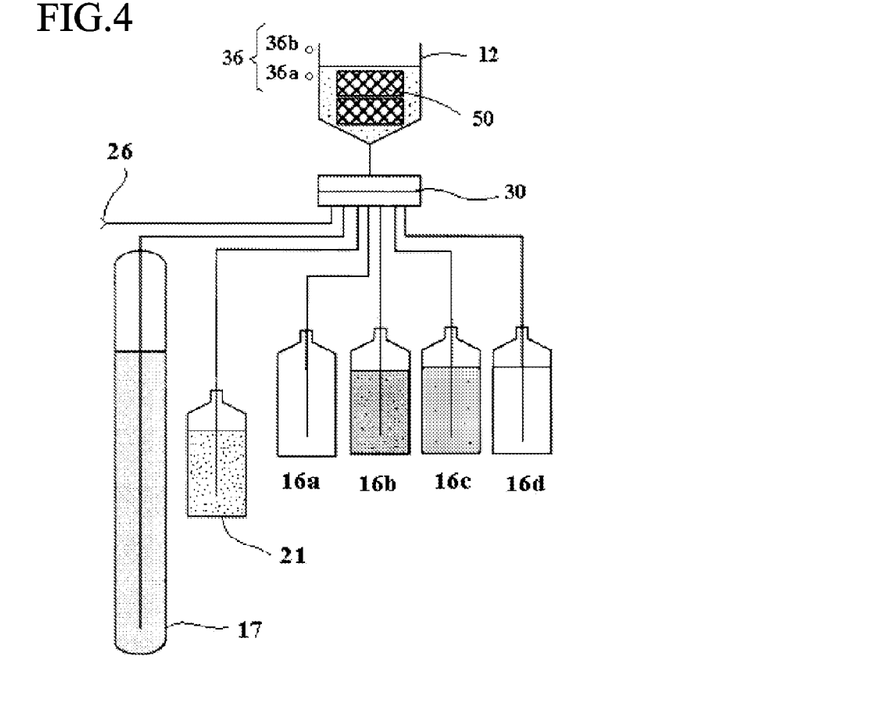
FIG. 4 is an explanation view of an infiltration treatment performed in the tissue treating apparatus shown in FIG. 1.

Next, the tissue specimens, which have been infiltration-treated in ethanol, are infiltrated in xylene so as to replace ethanol in the tissue specimens by xylene. Firstly, as shown in FIG. 4, the control unit 38 supplies xylene from the liquid-chemical reservoir 16a to the processing chamber 12 containing baskets 50, in which the tissue specimens have been contained, so as to infiltrate the tissue specimens in xylene. Then, xylene stored in the liquid-chemical reservoirs 16b, 16c and 16d are sequentially supplied to the processing chamber 12 so as to perform the infiltration treatment.

Next, the tissue specimens, which are stored in the processing chamber 12 and which have been infiltration-treated in xylene, are infiltrated in paraffin by sequentially supplying molten paraffin from the liquid-chemical reservoirs 18a-18d to the processing chamber 12. The xylene in the tissue specimens can be replaced by paraffin by the sequential infiltration in the molten paraffin.

After completing the infiltration treatment of the tissue specimens performed in paraffin, residual solids of paraffin are left in the processing chamber 12, so the inside of the processing chamber 12 is cleaned by using a xylene cleaning liquid stored in the second cleaning-liquid reservoir 21. The xylene, which has been used given times and has become useless in the tissue specimen infiltration treatment, is used as the xylene cleaning liquid. The xylene cleaning liquid includes ethanol from the tissue specimens, moisture therefrom, fragments of the tissue specimens, etc., but it has a sufficient cleaning (dissolving) ability for cleaning (dissolving) residual paraffin in the processing chamber 12.

Figure 5:
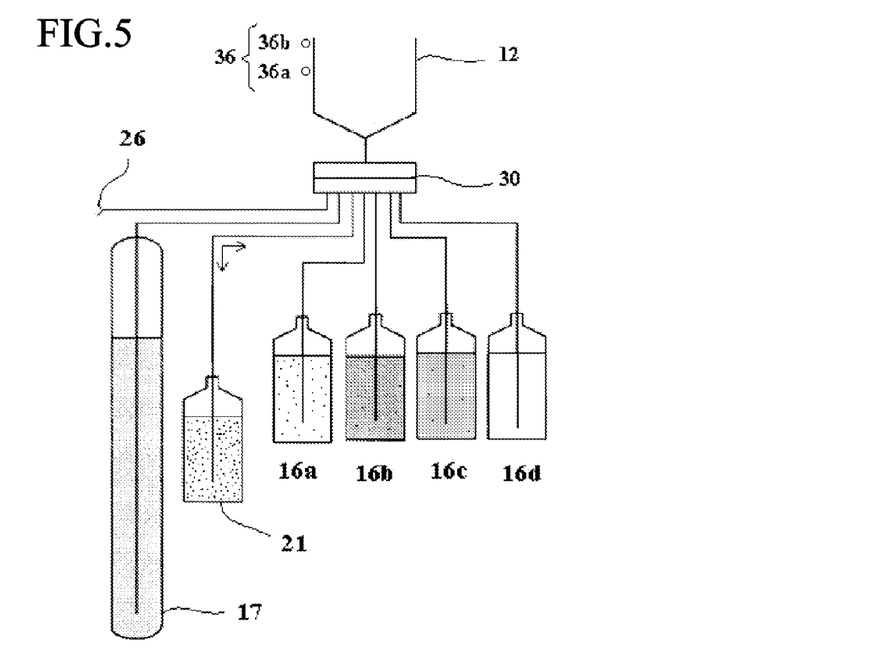
FIG. 5 is an explanation view of a cleaning operation for cleaning a processing chamber 12 of the tissue treating apparatus shown in FIG. 1.

When the inside of the processing chamber 12 is cleaned by the cleaning liquid stored in the second cleaning-liquid reservoir 21, the xylene cleaning liquid stored in the second cleaning-liquid reservoir 21 is supplied to the processing chamber 12 as shown in FIG. 5. Firstly, the control unit 38 actuates the pump 34 to reduce the inner pressure of the processing chamber 12, and then the xylene cleaning liquid stored in the second cleaning-liquid reservoir 21 is supplied to the processing chamber 12 via the rotary valve 30 and the open/close valve 32. While cleaning the processing chamber, the processing chamber 12 is heated by the heater 11, which is provided to an outer bottom face, so that the residual liquid chemical in the processing chamber 12 can be effectively removed and the cleaning ability of the xylene cleaning liquid can be improved by evaporating low-boiling components of ethanol, etc.

The xylene cleaning liquid, which has been used to clean the processing chamber 12 for a predetermined time, is returned to the second cleaning-liquid reservoir 21, via the open/close valve 32 and the rotary valve 30, by actuating the pump 34 to increase the inner pressure of the processing chamber 12.

Preferably, a heater is provided on an outer face of the second cleaning liquid reservoir 21 so as not to deposit paraffin in the second cleaning liquid reservoir 21, because xylene including residual paraffin remained in the processing chamber 12 is stored in the second cleaning liquid reservoir 21. By maintaining temperature of the xylene cleaning liquid, at given treatment temperature, in the second cleaning-liquid reservoir 21, a heating time of the heater 11, which heats the processing chamber 12, can be shortened.

After cleaning the inside of the processing chamber 12 by the xylene cleaning liquid stored in the second cleaning-liquid reservoir 21, residual xylene in the processing chamber 12 is removed by an ethanol cleaning liquid stored in the first cleaning-liquid reservoir 19. The ethanol cleaning liquid is constituted by ethanol which has been used given times and has become useless in the tissue specimen infiltration treatment. The ethanol cleaning liquid includes moisture from the tissue specimens, fragments of the tissue specimens, etc., but it has a sufficient cleaning (dissolving) ability for cleaning (dissolving) residual xylene in the processing chamber 12.

When the inside of the processing chamber 12 is cleaned by the ethanol cleaning liquid stored in the first cleaning-liquid reservoir 19, the control unit 38 of the cleaning means actuates the pump 34 to reduce the inner pressure of the processing chamber 12, and then the ethanol cleaning liquid stored in the first cleaning-liquid reservoir 19 is supplied to the processing chamber 12 via the rotary valve 30 and the open/close valve 32.

The ethanol cleaning liquid, which has been used to clean the processing chamber 12 for a predetermined time, is returned to the first cleaning-liquid reservoir 19, via the open/close valve 32 and the rotary valve 30, by actuating the pump 34 to increase the inner pressure of the processing chamber 12.

The processing chamber 12, in which the tissue specimens have been infiltrated in molten paraffin, is cleaned by the xylene cleaning liquid stored in the second cleaning-liquid reservoir 21, and then the processing chamber is cleaned by the ethanol cleaning liquid stored in the first cleaning-liquid reservoir 19, so new tissue specimens can be newly infiltration-treated, in the processing chamber 12, by ethanol, xylene and molten paraffin sequentially.

Figure 6A:
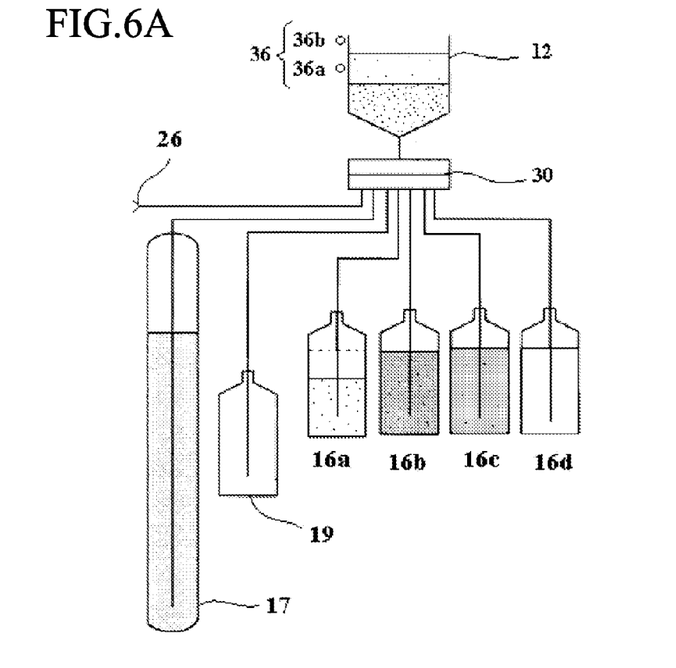
FIG. 6 is an explanation view explaining a supplementary operation which is performed when an amount of a cleaning liquid for cleaning the processing chamber 12 is insufficient.

When the xylene cleaning liquid stored in the second cleaning-liquid reservoir 21 is supplied to the processing chamber 12, if the xylene cleaning liquid does not reach the level-securing sensor 36a as shown in FIG. 6A, the control unit 38 actuates the rotary valve 30 and the pump 34 so as to supply xylene from the liquid-chemical reservoir 16a, in which the lowest-concentration xylene is stored, to the processing chamber 12. With this operation, the processing chamber 12 can be continuously cleaned by xylene, and new tissue specimens can be infiltration-treated, after cleaning the processing chamber, by ethanol stored in the first cleaning-liquid reservoir 19.

Figure 6B:
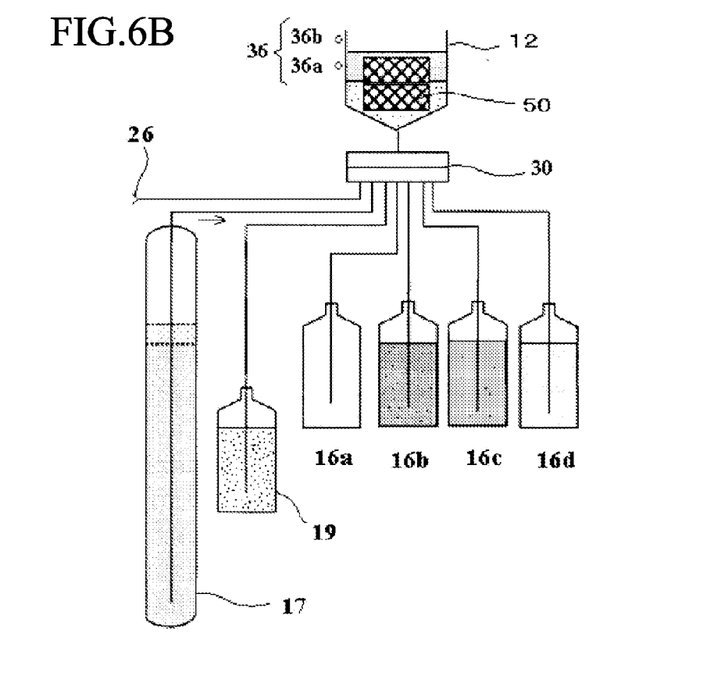

Note that, when the new tissue specimens are infiltration-treated, an amount of the liquid chemical supplied from the liquid-chemical reservoir 16a to the processing chamber 12 is insufficient as shown in FIG. 6B because xylene stored in the liquid-chemical reservoir 16a has been used for cleaning. In this case, as shown in FIG. 6B, new xylene of an amount corresponding to the insufficiency is supplied to the processing chamber 12 from the new chemical reservoir 17, so that the tissue specimen infiltration treatment can be continued.

FIGS. 6A and B show the infiltration treatment in xylene, control for performing the infiltration treatment in ethanol is similar to that in xylene, so detailed explanation will be omitted.

The xylene cleaning liquid stored in the second cleaning-liquid reservoir 21 is discarded after it has been used given times to clean the processing chamber 12 or the liquid chemical (xylene) stored in the liquid-chemical reservoir 16a has been used given times to perform the tissue specimen infiltration treatment.

Similarly, the ethanol cleaning liquid stored in the first cleaning-liquid reservoir 19 is discarded after it has been used given times to clean the processing chamber 12 or the liquid chemical (ethanol) stored in the liquid-chemical reservoir 14a has been used given times to perform the tissue specimen infiltration treatment.

In the tissue treating apparatus 10 shown in FIGS. 1-3, after the ethanol cleaning liquid stored in the first cleaning-liquid reservoir 19 or the xylene cleaning liquid stored in the second cleaning-liquid reservoir 21 is discarded outside, xylene or ethanol which has been used given times and has become useless in the tissue specimen infiltration treatment is reused as the cleaning liquid. In comparison with the conventional tissue treating apparatus in which the cleaning liquid and the liquid chemicals being useless in the tissue specimen infiltration treatment are discarded, the tissue treating apparatus 10 shown in FIGS. 1-3 is capable of reducing amounts of the liquid chemicals discarded and discarding the liquid chemicals easily.

Figure 7:
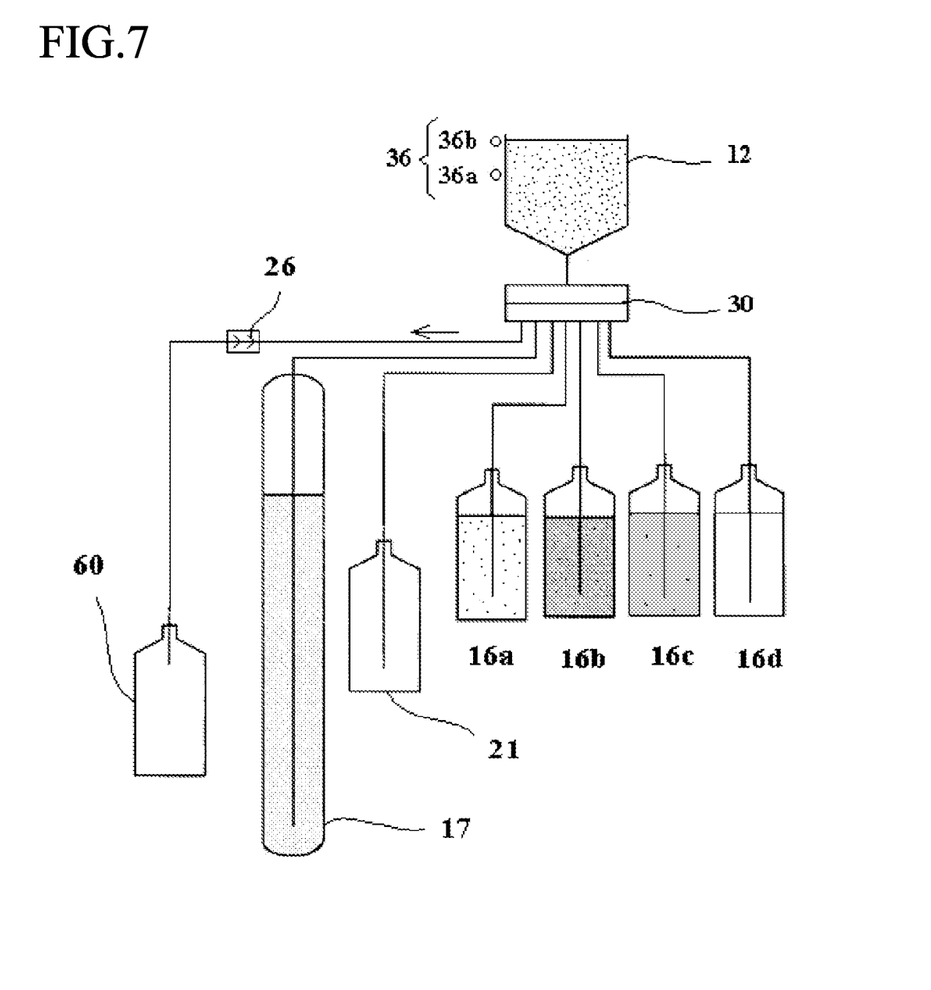
FIG. 7 is an explanation view explaining a discarding operation of xylene stored in a second cleaning-liquid reservoir 21.

Discarding the cleaning liquid from the cleaning-liquid reservoir will be explained with reference to FIG. 7. FIG. 7 is an explanation view showing a discarding operation of xylene stored in the second cleaning-liquid reservoir 21.

As shown in FIG. 7, an end of a tube extended from a drain reservoir 60 located outside of the tissue treating apparatus 10 is connected to a supply/discharge port 26, which constitutes discarding means and which is provided to a front face of the tissue treating apparatus 10.

Next, as shown in FIG. 7, the pump and the rotary valve 30, which constitute the discarding means, are actuated so as to supply all of the xylene cleaning liquid from the second cleaning-liquid reservoir 21 to the processing chamber 12 to clean the processing chamber 12, and then all of the cleaning liquid in the processing chamber 12 is discharged to the drain reservoir 60 via the rotary valve 30, etc.

Figure 8A:
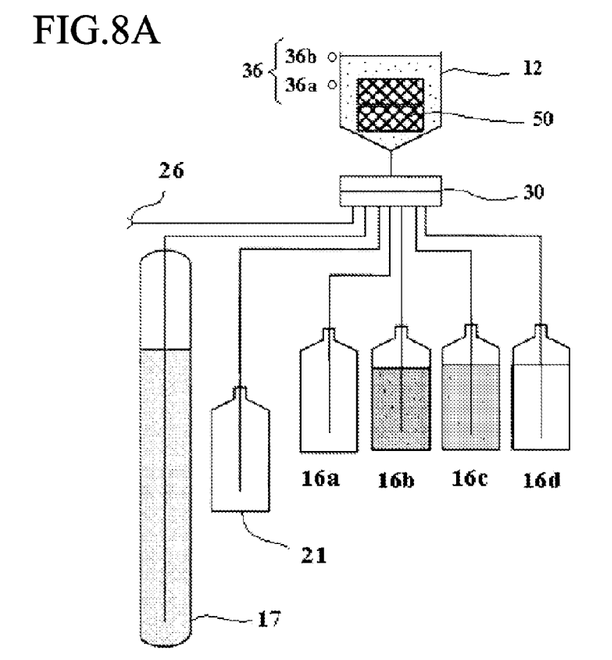
FIG. 8 is an explanation view explaining a transferring operation, in which liquid chemicals are sequentially transferred to the liquid-chemical reservoirs, from which the liquid chemical has been transferred to the second liquid-chemical reservoir 21, from other liquid-chemical reservoirs.

By discharging all of the cleaning liquid from the processing chamber 12, the processing chamber 12 gets empty. The most used liquid chemical (xylene) is transferred from the liquid-chemical reservoir 16a to the empty second cleaning-liquid reservoir 21 as the cleaning liquid. The liquid chemical is transferred by the above described transferring means. Firstly, as shown in FIG. 8A, all of the liquid chemical (xylene) in the liquid-chemical reservoir 16a is supplied to the processing chamber 12 to perform the tissue specimen infiltration treatment, and then the liquid chemical in the processing chamber 12 is discharged to the second cleaning-liquid reservoir 21, so that the liquid chemical in the liquid-chemical reservoir 16a can be transferred to the second cleaning-liquid reservoir 21.

Figure 8B:
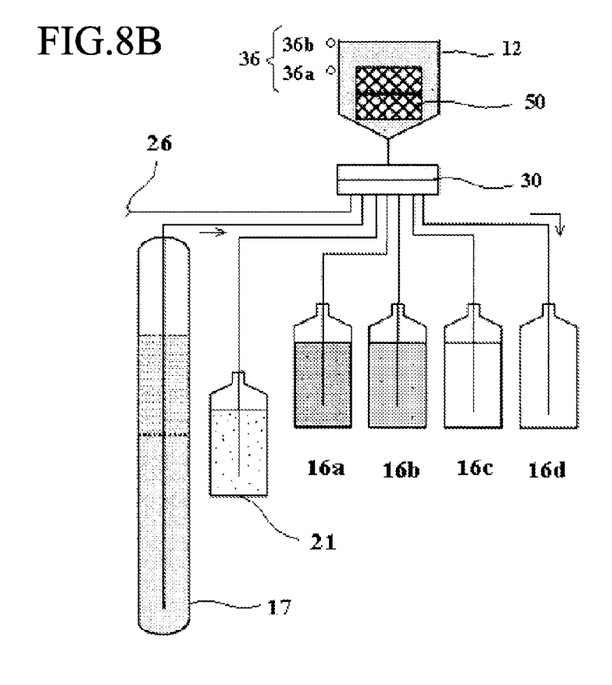

By transferring the all of the liquid chemical in the liquid-chemical reservoir 16a to the second cleaning-liquid reservoir 21, the liquid-chemical reservoir 16a gets empty, but the tissue specimen infiltration treatment is performed, in the processing chamber 12, by supplying the second-most-used liquid chemical from the liquid-chemical reservoir 16b, whose number of times being used is next to that of the liquid chemical stored in the liquid-chemical reservoir 16a, to the processing chamber 12 instead of the liquid chemical stored in the liquid-chemical reservoir 16a. Further, the tissue specimen infiltration treatment is performed by using the liquid chemical stored in the liquid-chemical reservoir 16c instead of the liquid chemical stored in the liquid-chemical reservoir 16b, and the tissue specimen infiltration treatment is performed by using the liquid chemical stored in the liquid-chemical reservoir 16d instead of the liquid chemical stored in the liquid-chemical reservoir 16c. Therefore, the tissue specimen infiltration treatment is performed by supplying the new liquid chemical (xylene) from the new chemical reservoir 17 to the processing chamber 12 instead of the liquid chemical stored in the liquid-chemical reservoir 16d as shown in FIG. 8B. The liquid chemical used in the infiltration treatment is transferred to the liquid-chemical reservoir 16d.

Note that, the discarding operation of the first cleaning-liquid reservoir 19 and the transferring operation for transferring the liquid chemical from the liquid-chemical reservoir 14a to the first cleaning-liquid reservoir 19 are similar to the discarding operation of the second cleaning-liquid reservoir 21 and the transferring operation for transferring the liquid chemical from the liquid-chemical reservoir 16a to the second cleaning-liquid reservoir 21, so explanation will be omitted.

In the above described tissue treating apparatus, when the liquid chemicals are transferred to the first cleaning-liquid reservoir 19 and the second cleaning-liquid reservoir 21 from the liquid-chemical reservoirs or when the cleaning liquids stored in the first cleaning-liquid reservoir 19 and the second cleaning-liquid reservoir 21 are discarded, the liquid chemicals and the cleaning liquids are transferred via the processing chamber 12, but they may be transferred, without passing through the processing chamber 12, via chemical transfer tubes or drain tubes.

In the above described embodiment, the cleaning liquids stored in the first cleaning-liquid reservoir 19 and the second cleaning-liquid reservoir 21, which are used for cleaning the processing chamber 12, are the liquid chemicals which have been used given times in the tissue specimen infiltration treatment performed in the processing chamber 12, further they may be used to clean the processing chamber 12 when the tissue treating apparatus which has been stopped is restarted.

What is claimed is:

1. A tissue treating apparatus, which supplies different kinds or different concentrations of liquid chemicals to and discharges the same, in a predetermined order, from a processing chamber containing a tissue specimen so as to perform a tissue specimen infiltration treatment, comprising:
   a processing chamber;
   a plurality of liquid-chemical reservoirs operable to store liquid chemicals to be used in the tissue specimen infiltration treatment;
   a cleaning-liquid reservoir operable to store a used liquid chemical which is a liquid chemical that has become useless in the tissue specimen infiltration treatment and which is usable as a cleaning liquid for removing a residual liquid chemical remaining in the processing chamber; and
   a valve operable to transfer (1) a liquid chemical from one of the plurality of liquid chemical reservoirs or a used liquid chemical from the cleaning-liquid reservoir to the processing chamber, and (2) a used liquid chemical from one of the plurality of liquid-chemical reservoirs to the cleaning-liquid reservoir.

2. The tissue treating apparatus according to claim 1, further comprising means for supplying a liquid chemical in an amount corresponding to an insufficiency of an amount of used liquid chemical supplied from the cleaning-liquid reservoir from one of the liquid chemical reservoirs in which the liquid chemical for the tissue specimen infiltration treatment is stored, when the amount of the used liquid chemical supplied from the cleaning-liquid reservoir to the processing chamber is insufficient.

3. The tissue treating apparatus according to claim 2, further comprising means for warming the liquid chemical stored in the cleaning-liquid reservoir.

4. The tissue treating apparatus according to claim 3, wherein ethanol, xylene and paraffin are used as the liquid chemicals for the tissue specimen infiltration treatment performed in the processing chamber, and the liquid chemicals are stored in the liquid-chemical reservoirs respectively,
   wherein an ethanol cleaning liquid, which is the ethanol useless in the tissue specimen infiltration treatment, is stored in a first cleaning-liquid reservoir, and a xylene cleaning liquid, which is the xylene useless in the tissue specimen infiltration treatment, is stored in a second cleaning-liquid reservoir, and
   wherein the valve is firstly operable to the xylene cleaning liquid stored in the second cleaning-liquid reservoir, and then the ethanol cleaning liquid stored in the first cleaning-liquid reservoir.

5. The tissue treating apparatus according to claim 2, wherein ethanol, xylene and paraffin are used as the liquid chemicals for the tissue specimen infiltration treatment performed in the processing chamber, and the liquid chemicals are stored in the liquid-chemical reservoirs respectively,
   wherein an ethanol cleaning liquid, which is the ethanol useless in the tissue specimen infiltration treatment, is stored in a first cleaning-liquid reservoir, and a xylene cleaning liquid, which is the xylene useless in the tissue specimen infiltration treatment, is stored in a second cleaning-liquid reservoir, and
   wherein the valve is firstly operable to transfer the xylene cleaning liquid stored in the second cleaning-liquid reservoir, and then the ethanol cleaning liquid stored in the first cleaning-liquid reservoir.

6. The tissue treating apparatus according to claim 1, further comprising means for warming the liquid chemical stored in the cleaning-liquid reservoir.

7. The tissue treating apparatus according to claim 6, wherein ethanol, xylene and paraffin are used as the liquid chemicals for the tissue specimen infiltration treatment performed in the processing chamber, and the liquid chemicals are stored in the liquid-chemical reservoirs respectively,
   wherein an ethanol cleaning liquid, which is the ethanol useless in the tissue specimen infiltration treatment, is stored in a first cleaning-liquid reservoir, and a xylene cleaning liquid, which is the xylene useless in the tissue specimen infiltration treatment, is stored in a second cleaning-liquid reservoir, and
   wherein the valve is firstly operable to transfer the xylene cleaning liquid stored in the second cleaning-liquid reservoir, and then the ethanol cleaning liquid stored in the first cleaning-liquid reservoir.

8. The tissue treating apparatus according to claim 1, wherein ethanol, xylene and paraffin are used as the liquid chemicals for the tissue specimen infiltration treatment performed in the processing chamber, and the liquid chemicals are stored in the liquid-chemical reservoirs respectively,
   wherein an ethanol cleaning liquid, which is the ethanol useless in the tissue specimen infiltration treatment, is stored in a first cleaning-liquid reservoir, and a xylene cleaning liquid, which is the xylene useless in the tissue specimen infiltration treatment, is stored in a second cleaning-liquid reservoir, and
   wherein the valve is firstly operable to transfer the xylene cleaning liquid stored in the second cleaning-liquid reservoir, and then the ethanol cleaning liquid stored in the first cleaning-liquid reservoir.

* * * * *